US006455069B1

(12) United States Patent
Michaud et al.

(10) Patent No.: US 6,455,069 B1
(45) Date of Patent: Sep. 24, 2002

(54) DIRECTLY COMPRESSIBLE STARCH AS ENHANCER OF PROPERTIES OF EXCIPIENTS WHEN USED AS BINDER AND DISINTEGRANT FOR COMPRESSION TABLETS

(75) Inventors: Jacques Loïc Marie Michaud, Brussels (BE); Liesbeth Maria Fernande Meeus, Kortenberg (BE)

(73) Assignee: Cerestar Holding B.V., Sas van Gent (NL)

( * ) Notice: Subject to any disclaimer, the term of this patent is extended or adjusted under 35 U.S.C. 154(b) by 3 days.

(21) Appl. No.: 09/604,299

(22) Filed: Jun. 26, 2000

(30) Foreign Application Priority Data

Jun. 26, 1999 (GB) ............................................. 9914936

(51) Int. Cl.$^7$ .............................. A61K 9/20; A61K 9/00
(52) U.S. Cl. ........................ 424/464; 424/400; 424/439; 424/465; 424/489; 514/948; 514/951; 514/960
(58) Field of Search ................................. 424/400, 439, 424/464, 465, 489; 514/948, 951, 960

(56) References Cited

U.S. PATENT DOCUMENTS

| 3,034,911 A | 5/1962 | McKee et al. |
| 3,490,742 A | 1/1970 | Nichols et al. |
| 3,622,677 A | 11/1971 | Short et al. |
| 3,956,515 A | 5/1976 | Moore et al. |
| 4,072,535 A | 2/1978 | Short et al. |
| 4,369,308 A | 1/1983 | Trubiano |
| 4,383,111 A | 5/1983 | Takeo et al. |
| 4,384,005 A | 5/1983 | McSweeney |
| 4,551,177 A | 11/1985 | Trubiano et al. |
| 4,600,579 A | * 7/1986 | Salpekar et al. .............. 424/80 |
| 5,164,014 A | 11/1992 | Brancq et al. |

FOREIGN PATENT DOCUMENTS

| EP | 0 130 683 | 1/1985 |
| EP | 0 402 186 | 12/1990 |
| EP | 0 933 079 | 8/1999 |
| GB | 1 216 873 | 12/1970 |

OTHER PUBLICATIONS

Maudhane et al., Tableting Properties of a Directly Copressible Starch, Journal of Pharmaceutical Sciences, vol. 58, No. 5, May 1969, pp. 616–620.
Wierik et al., High Surface Area Starch Products as Filler–Binder in Direct Compression Tablets, Pharmazie, 51 (1996) May 5, 1996, pp. 311–315.
Patent Abstracts of Japan, vol. 7, No. 114 (c–166), May 18, 1983 (1983–05–18) & JP 58 032828 a (Ajinomoto KK).

* cited by examiner

Primary Examiner—Thurman K. Page
Assistant Examiner—Charesse L. Evans
(74) Attorney, Agent, or Firm—Fitch, Even, Tabin & Flannery

(57) ABSTRACT

The present invention relates to a mixture of a starch and at least one other excipient for tabletting wherein the starch is free-flowing compressible processed starch powder suitable for use both as a binder and as a disintegrant in tablets. The free-flowing starch powder improves the characteristics and the properties of the tablets when mixed with one or more different excipients.

The present invention also discloses a method for obtaining tablets comprising the free-flowing compressible processed starch together with at least one excipient and the tablets obtained by such a method.

20 Claims, 4 Drawing Sheets

(4 of 4 Drawing Sheet(s) Filed in Color)

FIGURE 1a

THE INFLUENCE OF THE COMPOSITION OF THE MIXTURE ON THE TENSILE STRENGTH.
(for tablets made with a compression force of 25kN)
Type of fit: Quadratic smoothing ($R^2 = 0.9967$)

Vertices: MCC: Avicel PH-102 (FMC); directly compressible processed starch powder; Lactose: Flowlac 100 (Meggle)

Tensile strength (N/mm$^2$): 3, 4, 5, 6, 7, 8, 9, 10, 11, above

FIGURE 1b

THE INFLUENCE OF THE COMPOSITION OF THE MIXTURE ON THE TENSILE STRENGTH.
(for tablets made with a compression force of 25kN)
Type of fit: Quadratic smoothing ($R^2 = 0.9979$)

Vertices: MCC: Avicel PH-102 (FMC); Starch 1500 (Colorcon); Lactose: Flowlac 100 (Meggle)

Tensile strength (N/mm$^2$): 3, 4, 5, 6, 7, 8, 9, 10, 11, above

FIGURE 2a

THE INFLUENCE OF THE COMPOSITION OF THE MIXTURE ON THE DISINTEGRATION TIME.
( for tablets made with a compression force of 25 kN )
Type of fit: Special cubic smoothing ($R^2$= 0.8502)

MCC: Avicel PH-102
(FMC)

Disintegration time (sec)
- 240
- 300
- 360
- 420
- 480
- 540
- 600
- 660
- 720
- above directly compressible
processed starch powder Lactose: Flowlac 100
(Meggle)

FIGURE 2b

THE INFLUENCE OF THE COMPOSITION OF THE MIXTURE ON THE DISINTEGRATION TIME.
( for tablets made with a compression force of 25kN )
Type of fit: Quadratic smoothing ($R^2$= 0.9752)

MCC: Avicel PH-102
(FMC)

Disintegration time (sec)
- 240
- 300
- 360
- 420
- 480
- 540
- 600
- 660
- 720
- above Starch 1500
(Colorcon)

Lactose: Flowlac 100
(Meggle)

DIRECTLY COMPRESSIBLE STARCH AS ENHANCER OF PROPERTIES OF EXCIPIENTS WHEN USED AS BINDER AND DISINTEGRANT FOR COMPRESSION TABLETS

TECHNICAL FIELD

This invention relates to a mixture of a starch and an excipient for tabletting wherein the starch is free-flowing compressible processed starch powder suitable for use both as a binder and as a disintegrant in tablets. The free-flowing starch powder improves the characteristics and the properties of the tablets when mixed with one or more different excipients.

The present invention also discloses a method for obtaining tablets comprising the free-flowing compressible processed starch together with at least one excipient and the tablets obtained by such a method.

BACKGROUND OF THE INVENTION

Tablets are one of the most frequently employed delivery forms for most medicinal preparations. This situation can be explained by the fact that this dosage form allows a good accuracy of dosage of the active component of the medicinal formulation. Furthermore handling and packaging are a lot easier and conservation and stability of these preparations are generally better than those of other formulations.

The same arguments also explain the reason why tablets are often used as media for other applications such as food, including confectionery products, aromas or sweeteners, detergents, dyes or phytosanitary products.

Tablets can be manufactured using three main processes, wet granulation, dry granulation and direct compression.

In wet granulation, components are typically mixed and granulated using a wet binder, the wet granulates are then sieved, dried and eventually ground prior to compressing the tablets.

In dry granulation, powdered components are typically mixed prior to being compacted, also called pre-compression, to yield hard slugs which are then ground and sieved before the addition of other ingredients and final compression.

Direct compression is now considered to be the simplest and the most economical process for producing tablets. This process requires only two steps; i.e., the mixing of all the ingredients and the compression of this mixture.

A component of a tablet is usually defined as being either an excipient or an active ingredient. Active ingredients are normally ones that trigger a pharmaceutical, chemical or nutritive effect and they are present only up to the strict limit necessary for providing this effect in the right proportion. Excipients are chemically and pharmaceutically inert ingredients that are included to facilitate the preparation of the dosage forms or to adapt the release of the active ingredients.

Excipients can be characterised according to their function during the formulation as, for instance, binders, disintegrants, fillers (or diluents), glidants, lubricants and eventually flavours, sweeteners and dyes.

Lubricants are intended to improve the ejection of the compressed tablet from the die of the tablet-making equipment.

Glidants are added to improve the powder flow. They are typically used to help the mixture of all the components to fill evenly and regularly the die before the compression.

Fillers are inert ingredients sometimes used as bulking agents in order to decrease the concentration of the active ingredient in the final formulation. The binders in many cases also provide the function of filler.

Disintegrants may be added to formulations in order to help the tablets disintegrate when they are placed in a liquid environment and so release the active ingredient. The disintegration properties are, mostly, based upon the ability of the disintegrant to swell in the presence of a fluid, such as water or gastric juice. This swelling disrupts the continuity of the tablet structure and thus, allows the different components to enter into solution or into suspension. Commonly used disintegrants include native starches, modified starches, modified cellulose, microcrystalline cellulose or alginates.

Binders are used to hold together the structure of the dosage forms. They have the property to bind together all the other ingredients after sufficient compression forces have been applied and they provide the integrity of the tablets.

Starches are known to act in some cases as binders and in some other cases as disintegrants according to the fact that they are native, chemically modified or physically modified.

Native granular starches and, to a smaller extent, cooked starches (also referred to as pregelatinised starches) can show somewhat limited binding capacities when employed in direct compression. Cooked starches, even when they are satisfactory as binders are not satisfactory in terms of disintegration. These starches do not really disperse, they show the tendency to prevent the penetration of water into the tablet, thus preventing its disintegration, by forming a tacky film on its surface.

EP-A-0402186 describes a directly compressible starch mixture obtained by mixing 1 to 20% of a starch paste with 99–80% of native starch. The starch paste is obtained by treating native starch at 85° C., which results in breaking of the starch granules.

Partially cold water swellable starches for use as binders and/or disintegrants in the manufacture of tablets by direct compression and as fillers for formulations supplied in hard gelatine capsules, are described in U.S. Pat. No. 3,622,677 and U.S. Pat. No. 4,072,535. The material described is essentially a pre-compacted starch powder obtained by subjecting a non-gelatinised granular starch to physical compaction between steel rollers with the possible input of thermal energy. The compacted starch shows the presence of sharp birefringent granules and non-birefringent granules as well as some aggregates of granules and fragments dried to a moisture content of 9–16%. After the compactation the starch is ground and sieved to yield a free-flowing powder. The above mentioned starch powders exhibit limited binding capacity in direct compression and poor disintegration properties. Formulations of active ingredients prepared using that kind of excipient are described, for instance in EP-A-0,130, 683 for N-acetyl-p-aminophenol.

Other cold water swellable physically modified starches are described as being useful as disintegrant but with very poor binding properties (see U.S. Pat. No. 4,383,111). In that case, the granular starch is cooked in the presence of water and possibly an organic solvent at temperature not higher than 10° C. higher than its gelatinisation temperature. The so-obtained starch is then dried resulting in non-birefringent granules. Mixtures containing cold water swellable starch are describe for food application i.e. U.S. Pat. No. 3,956,515 for the preparation of starch batter for meat pieces.

Chemical modification of starch has also been investigated. Crosslinked pregelatinised starches such as starch phosphates, starch adipates, starch sulphates, starch glycolates or carboxymethyl starches are useful as disintegrants although they exhibit poor binding capacities (see U.S. Pat. No. 3,034,911 and U.S. Pat. No. 4,369,308).

Acid and enzyme hydrolysed starches are reported to be useful as binders (U.S. Pat. No. 4,551,177). These compressible starches are prepared by treating a granular starch with an acid and/or alpha-amylase enzyme at a temperature below the gelatinisation temperature of the starch. These treated starches show altered and weakened granules with disrupted surfaces. These starches are said to be useful as binders for tabletting as well as binders and fillers for capsule filling and are said to exhibit reasonable disintegration properties.

Dextrinised starches (see U.S. Pat. No. 4,384,005) and starch fractions such as non-granular amylose (see U.S. Pat. No. 3,490,742) are also described as having limited binding and/or disintegration properties. These are of limited interest due to the expensive processes needed for their preparation.

Co-pending European patent application ep 99300571.9 describes a free-flowing directly compressible processed starch powder suitable for use as a binder in direct compression processes yielding very hard tablets at relatively low compression forces as well as for use as a binder and/or filler in the preparation of capsule dosage forms.

Tablets resulting from the compression of the above-mentioned starch disintegrate in an aqueous medium at a high speed and, additionally, exhibit a low friability pattern. This directly compressible starch powder is useful as a binder and/or a disintegrant for tablets prepared by direct compression, wet granulation or dry granulation. It is also useful as a binder and as a filler in the process of filling capsules.

This co-pending patent application is herein incorporated by reference.

SUMMARY OF THE INVENTION

The present invention discloses a composition for forming a tablet or other unit dosage form comprising regular and smooth partially-swollen non-birefrigent granules of starch, together with non-swollen birefrigent granules of starch wherein the ratio of non-swollen birefrigent granules to swollen non-birefrigent granules is in the range of from 1:5 to 5:1 and at last one other excipient. The other excipient may be a binder, filler or disintegrant. The starch typically has an average particle size greater than 50 $\mu$m and a moisture content of from 3 to 15% by weight. To be of practical use the composition further comprises an active ingredient.

The active ingredient is present in an amount which is effective to perform its desired function and is typically present in an amount of from 0.01 to 80% (w/w).

The other excipient is at least one compound but it may be between 1 and 10. Typical excipients are chosen from the group consisting of starch, pregelatinised starch, polyvinylpyrrolidone, methylcellulose, microcrystalline cellulose, dicalcium phosphate, tricalcium phosphate, calcium carbonate, calcium sulphate, lactose, dextrose, sucrose, sorbitol and mannitol or mixtures thereof.

The ratio of the directly compressible starch and the (other) excipient is dependent on the type of use one wants to make of the tablet typically it is between 1:10 and 10:1.

The present invention also discloses a method for obtaining tablets comprising the directly compressible processed starch together with the at least one (other) excipient.

The present inventions further discloses tablets comprising regular and smooth partially-swollen non-birefrigent granules of starch, together with non-swollen birefrigent granules of starch wherein the ratio of non-swollen birefrigent granules to swollen non-birefrigent granules is in the range of from 1:5 to 5:1 and at last one other excipient. Such tablets preferably contain an active ingredient.

BRIEF DESCRIPTION OF THE FIGURES

The file of this patent containing at least one drawing executed in color.

All figures are ternary graphs obtained by the response surface method and showing the relationship between the ratio of the excipients and the specified tablet characteristics.

FIGS. 1a and 1b show the influence of the composition of the mixture of microcrystalline cellulose (MCC): Avicel® PH-102, Lactose : Flowlac® 100 and directly compressible processed starch powder, respectively Starch 1500 on the tensile strength.

FIGS. 2a and 2b show the influence of the same compositions as demonstrated in FIGS. 1a and 1b, this time on the disintegration time.

DETAILED DESCRIPTION OF THE INVENTION

Figure 3A:
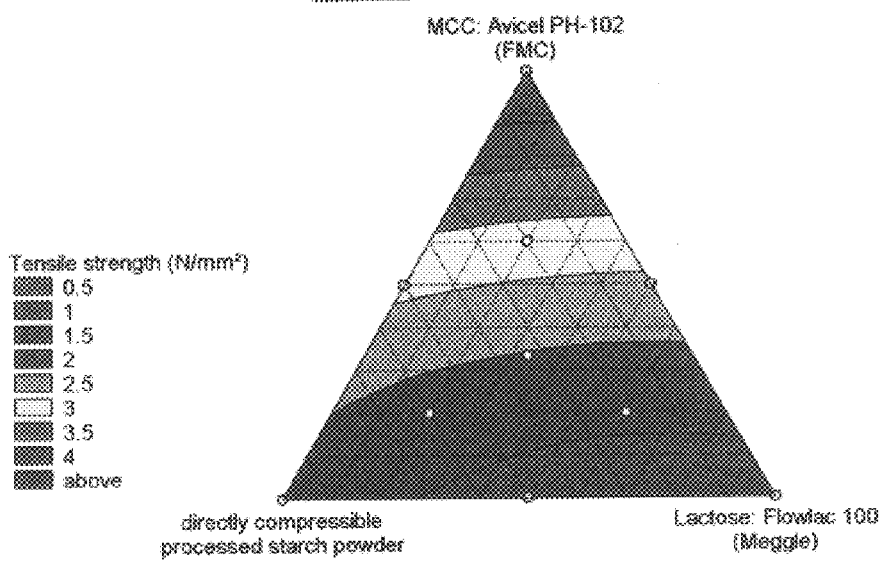
FIGS. 3a and 3b show the influence of the composition of the mixture of microcrystalline cellulose (MCC): Avicel® PH-102, Lactose : Flowlac® 100 and directly compressible processed starch powder, respectively Starch 1500 on the tensile strength when the excipient mixture is used together with paracetamol as an active ingredient in a weight ratio of excipient mixture paracetamol=60:40.

Co-pending non-prepublished European patent application ep 99300571.9 discloses a new type of directly compressible starch powder. This starch powder is characterised in that it comprises regular and smooth partially-swollen granules of starch wherein the ratio of non-swollen birefrigent granules to swollen non-birefrigent granules is in the range of from 1:5 to 5:1. The starch powder is further characterised in it has an average particle size greater than 50 $\mu$m and a moisture content of from 3 to 15% by weight.

The starch powder can be obtained by a process comprising the following steps; 1) preparing a slurry of starch in water, 2) heating the slurry to a temperature not substantially higher than the gelatinisation temperature of the starch to cause partial swelling of the starch granules without causing disruption of the starch granules, 3) cooling the starch slurry to prevent any further swelling of the starch granules and 4) spray-drying the cooled slurry to produce a free-flowing starch powder having a moisture content of from 3 to 15% by weight.

The use of this starch powder as a binder, disintegrant or filler for hard tablets and capsules is also disclosed.

We have previously shown that this directly compressible starch powder can be used as binder-disintegrant for making tablets.

The present invention discloses that the directly compressible processed starch powder is used in combination with at least one other excipient. The other excipient being a binder, filler or disintegrant. The combinations of starch and excipient are used at any useful ratio. Even though the possibility to prepare formulations using only one multifunctional excipient is a clear advantage, most of the existing formulations comprise mixes of several binders. Commonly used compression binders or disintegrants include pregelatinised starches, starches, polyvinylpyrrolidone, methylcellulose, microcrystalline cellulose, dicalcium phosphate, tricalcium phosphate, calcium carbonate, calcium sulphate, lactose, dextrose, sucrose, sorbitol or mannitol. Blends of several of these excipients, usually two to three, allows the investigation of possible synergies with the active ingredient in order to optimise the hardness of tablets at the same time as their disintegration time.

According to the present invention there is provided the use of the directly compressible processed starch powder described in co-pending European patent application ep 99300571.9 as binder and disintegrant as mixed together with other excipients such as binders, fillers or disintegrants, usually 1 to 10 and preferably 2, for tablets prepared by direct compression, wet granulation or dry granulation.

The embodiment of the present invention comprises a composition for the formulation of tablets prepared either by direct compression or by dry or wet granulation, containing the above-mentioned starch powders referred to as directly compressible starch powders together with at least one other excipeint (binder, filler or disintegrant) and at least one active material. The other binders can be chosen for instance from polyvinylpyrrolidone, methylcellulose, microcrystalline cellulose, dicalcium phosphate, tricalcium phosphate, calcium carbonate, calcium sulphate, lactose, dextrose, sucrose, sorbitol or mannitol. This formulation can include any active ingredient in suitable proportion.

Tablets obtained according to the present invention from blends of 1 to 10 binders in any proportion with the directly compressible starch powder are characterised by the fact that they show significantly higher hardness at any compression forces than the same formulation with other starches. At the same time they are also capable of disintegrating in an aqueous medium at significantly higher speed than the disintegration speed of tablets made from each single individual component. Useful dosage of the blend of binders including directly compressible starch powders of the invention varies depending upon active ingredients and other excipients and can be between 2 to 95% (w/w).

To be of practical use the tablets of the present invention will contain an active ingredient. The active ingredient may be any drug i.e. a pharmaceutically active material, usually delivered in tablet or capsule form. This includes for instance analgesics, antipyretics, anti-inflammatory agents, vitamins, antibiotics, hormones, steroids, tranquilisers, or sedatives. Other active materials that can be included into tablets can also be formulated with the free-flowing compressible processed starch. This triggers applications in food including confectionery products. Other "active" ingredients are aromas, sweeteners, detergents, enzymes and other proteins, dyes, fertilisers or herbicidal products.

The amount of the ingredient will depend on its activity. When present in substantial amounts the physical or chemical characteristics of the ingredient may influence the characteristics of the tablets. In general the active ingredient will be present in the tablet in amounts of from 0.01 to 80% (w/w).

In order to illustrate the present invention the following examples are provided.

The first example demonstrates that the directly compressible processed starch powder described in co-pending European patent application ep 99300571.9 improves the properties of tablets, which are produced from mixtures of direct compressible starch, lactose and microcrystalline cellulose by direct compression, when compared with the same tablets produced under identical conditions but with the commercial Starch 1500 as excipient.

At all tested compositions and at all compositions calculated for obtaining the ternary graphs it is shown that first of all suitable tablets are obtained from the mixture of directly compressible starch, microcrystalline cellulose and lactose and second that these tablets are better than when commercial Starch 1500 was used. The following parameters were tested; tensile strength, friability and disintegration time (at fixed compression force).

It was unexpectedly found that when tablets were made using directly compressible processed starch compared with Starch 1500 the tablets were harder, the friability was lower and the disintegration time was faster.

In the second example the same parameters were determined as in the first example. It was demonstrated that the directly compressible processed starch powder improves the properties of tablets, which are produced from mixtures of direct compressible starch, lactose and microcrystalline cellulose as excipients and 40% Paracetamol as active ingredient by direct compression.

Additionally the example demonstrates that the tablets obtained from mixtures of the directly compressible processed starch powder and other excipients have better properties compared to tablets obtained from mixtures of a conventional compressible starch and other excipients in the same conditions when Paracetamol is formulated with them.

EXAMPLE 1

This example demonstrates that the directly compressible processed starch powder described in co-pending European patent application ep 99300571.9 improves the properties of tablets, which are produced from mixtures of direct compressible starch, lactose and microcrystalline cellulose by direct compression. Additionally the example demonstrates that the obtained tablets from mixtures of the directly compressible processed starch powder described in co-pending European patent application ep 99300571.9 and other excipients still have better properties compared to tablets obtained from mixtures of a conventional compressible starch and other excipients in the same conditions.

All excipients were sieved over a 0.8 mm sieve. Equal quantities of the excipients were mixed following the dilution method in a low-shear drum mixer for 10 min at 12 rpm. Than 0.25% $SiO_2$ (Aerosil 200—Degussa) and the possible remaining of the excipients were added and blended for 15 min at 12 rpm. Afterwards 0.50% MgSt (Pharmachemic Tramedico) was added and blended for 3 min at 12 rpm. Round flat-faced tablets were compressed on a triple punch rotative tabletting press (Korch) operating at 40 rpm. The produced tablets have a surface of $1cm^2$ and a target weight of 350 mg. The dimensions of the tablets and the hardness were measured with a tablet tester (ERWEKA, Model TBH). The friability of the tablets was determined on a friability tester (Pharmatest). The disintegration time was measured at 37° C. with a disintegration machine (Pharmatest). The results are summarised as shown in tables 1 to 3.

TABLE 1

| Ratio of excipients | | | Tensile strength (N/mm²) at compression force 25kN | |
|---|---|---|---|---|
| MCC: Avicel PH-102 (FMC) | LACTOSE: Flowlac 100 (Meggle) | DC STARCH | With processed white maize starch* as DC Starch | With Starch 1500 ™ ** (Colorcon) as DC Starch |
| 0 | 1.0 | 0 | 5.6 | 5.6 |
| 0 | 0 | 1.0 | 6.7 | 2.0 |
| 0 | 0.50 | 0.50 | 5.0 | 2.9 |
| 0.50 | 0 | 0.50 | 8.6 | 6.1 |
| 0.50 | 0.50 | 0 | 8.4 | 8.4 |
| 0.20 | 0.20 | 0.60 | 6.4 | 4.0 |
| 0.20 | 0.60 | 0.20 | 6.2 | 5.1 |
| 0.60 | 0.20 | 0.20 | 9.1 | 7.6 |
| 0.33 | 0.33 | 0.34 | 7.0 | 5.4 |

*A processed white maize starch as described in co-pending European patent application ep 99300571.9
**Starch 1500 ™ HM from Colorcon Company Table 1 shows that tablets made from mixtures containing microcrystalline cellulose, lactose and the direct compressible processed starch described in co-pending European patent application ep 99300571.9 show in all mixed proportions significantly higher tensile strengths than tablets made from mixtures containing microcrystalline cellulose, lactose and a standard direct compressible starch (Starch 1500 HM). Furthermore, mixtures of microcrystalline cellulose and the direct compressible processed starch described in co-pending European patent application yield tablets with higher tensile strengths than mixtures containing microcrystalline cellulose and lactose in respectively the same proportion. It is remarkable to notice that tablets made from mixtures of microcrystalline cellulose and a standard direct compressible starch (Starch 1500 HM) show lower tensile strengths than tablets made from mixtures of microcrystalline cellulose and lactose in respectively the same proportion.

This demonstrates that the directly compressible processed starch described in co-pending European patent application ep 99300571.9 improves the quality of tablets in terms of hardness when it is used in mixtures with other excipients.

TABLE 2

| Ratio of excipients | | | Friability (%) at compression force 25kN | |
|---|---|---|---|---|
| MCC: Avicel PH-102 (FMC) | LACTOSE: Flowlac 100 (Meggle) | DC STARCH | With processed white maize starch* as DC Starch | With Starch 1500 ™ ** (Colorcon) as DC Starch |
| 1.0 | 0 | 0 | 0.1 | 0.1 |
| 0 | 1.0 | 0 | 1.0 | 1.0 |
| 0 | 0 | 1.0 | <0.1 | 0.4 |
| 0 | 0.50 | 0.50 | 0.1 | 0.3 |
| 0.50 | 0 | 0.50 | <0.1 | 0.1 |
| 0.50 | 0.50 | 0 | 0.1 | 0.1 |
| 0.20 | 0.20 | 0.60 | 0.1 | 0.2 |
| 0.20 | 0.60 | 0.20 | 0.2 | 0.2 |
| 0.60 | 0.20 | 0.20 | <0.1 | <0.1 |
| 0.33 | 0.33 | 0.34 | 0.1 | 0.1 |

*A processed white maize starch as described in co-pending European patent application ep 99300571.9
**Starch 1500 ™ standard moisture from Colorcon Company Table 2 shows that tablets made from mixtures containing microcrystalline cellulose, lactose and the direct compressible processed starch described in co-pending European patent application ep 99300571.9 show in all tested proportions significantly lower friability than tablets made from mixtures containing microcrystalline cellulose, lactose and a standard direct compressible starch (Starch 1500 HM). As expected, microcrystalline cellulose and the direct compressible processed starch described in co-pending European patent application ep 99300571.9 yield as well tablets with lower friability than mixtures containing microcrystalline cellulose and lactose in respectively the same proportion. It is also remarkable to notice that tablets made from mixtures of microcrystalline cellulose and a standard direct compressible starch (Starch 1500 HM) show higher friability than tablets made from mixtures of microcrystalline cellulose and lactose in respectively the same proportion.

This demonstrates that the directly compressible processed starch described in co-pending European patent application ep 99300571.9 does not increase or even improves the quality of tablets in terms of friability when it is used in mixtures with other excipients. Therefore tablet integrity is better maintained during the process and the transport.

TABLE 3

| Ratio of excipients | | | Disintegration time (sec) at compression force 25kN | |
|---|---|---|---|---|
| MCC: Avicel PH-102 (FMC) | LACTOSE: Flowlac 100 (Meggle) | DC STARCH | With processed white maize starch* as DC Starch | With Starch 1500 ™ ** (Colorcon) as DC Starch |
| 1.0 | 0 | 0 | 600 | 600 |
| 0 | 1.0 | 0 | 570 | 570 |
| 0 | 0 | 1.0 | 520 | 1850 |
| 0 | 0.50 | 0.50 | 300 | 440 |
| 0.50 | 0 | 0.50 | 220 | 730 |
| 0.50 | 0.50 | 0 | 700 | 700 |
| 0.20 | 0.20 | 0.60 | 340 | 870 |
| 0.20 | 0.60 | 0.20 | 200 | 300 |
| 0.60 | 0.20 | 0.20 | 310 | 380 |
| 0.33 | 0.33 | 0.34 | 260 | 460 |

*A processed white maize starch as described in co-pending European patent application ep 99300571.9
**Starch 1500 ™ standard moisture from Colorcon Company Table 3 shows that tablets made from mixtures containing microcrystalline cellulose, lactose and the direct compressible processed starch described in co-pending European patent application ep 99300571.9 show in all tested proportions significantly faster disintegration time than tablets made from mixtures containing microcrystalline cellulose, lactose and a standard direct compressible starch (Starch 1500 HM). Microcrystalline cellulose and the direct compressible processed starch described in co-pending European patent application ep 99300571.9 yield tablets with extremely faster disintegration time than mixtures containing microcrystalline cellulose and lactose in respectively the same proportion and especially for mixtures of microcrystalline cellulose and the direct compressible processed starch described in co-pending European patent application ep 99300571.9 in the range of 0.75/0.25 to 0.25/0.75. Tablets made from mixtures of microcrystalline cellulose and a standard direct compressible starch (Starch 1500 HM) show higher disintegration time as long as more than 50% of starch are present in the mixture than tablets made from mixtures of microcrystalline cellulose and lactose in respectively the same proportion.

This demonstrates that the directly compressible processed starch described in co-pending European patent application ep 99300571.9 significantly improves the quality of tablets in terms of faster disintegration time when it is used in mixtures with other excipients resulting in a faster liberation of the active ingredient after ingestion of the tablet.

The results of tables 1 and 3 can be more easily illustrated by ternary graphs as shown in FIGS. 1 to 2. These ternary graphs are particularly helpful to examine the influence of the composition of the mixture on a pharmaceutical formulation. Response surface method is used to characterise the relationship between the ratio of excipients and the different tablet properties. The method and the resulting graphs are also a particularly powerful tool to identify potential synergies between the components of the mixtures.

FIG. 1a compared with FIG. 1b shows that tablets made from a mixture where besides microcrystalline cellulose and/or lactose also the directly compressible processed starch as described in co-pending European patent application ep 99300571.9 is used, reaches in all the points a higher tensile strength than when a mixture where besides microcrystalline cellulose and/or lactose also a standard compressible starch is used. It is remarkable to notice that in FIG. 1a, the limiting factor in term of tensile strength of tablet is the proportion of lactose whereas, in FIG. 1b, this limiting factor is by far the proportion of standard direct compressible starch. This trend can also be noticed from the different orientation of the lines on each ternary graph.

FIG. 2a compared with FIG. 2b shows that tablets made from a mixture where besides microcrystalline cellulose and/or lactose also the directly compressible processed starch as described in co-pending European patent application ep 99300571.9 is used, reaches in all the points a lower disintegration time than when a mixture where besides microcrystalline cellulose and/or lactose also a standard compressible starch is used.

It is also remarkable to notice that in FIG. 2b, the limiting factor in term of disintegration time of tablet is by far the proportion of standard direct compressible. On the contrary, FIG. 2a reveals an important synergetic effect when the directly compressible processed starch as described in co-pending European patent application ep 99300571.9 is used in the formulation. The fastest disintegration time (in most cases inferior or equal to 300 sec.) is achieved when formulations contain 25% till 75% of the directly compressible processed starch as described in co-pending European patent application ep 99300571.9 whatever is the remaining proportion of lactose and microcrystalline cellulose. Disintegration times of less than 300 sec. are practicaly never reach when formulations contain standard direct compressible instead of of the directly compressible processed starch as described in co-pending European patent application ep 99300571.9.

EXAMPLE 2

This example demonstrates that the directly compressible processed starch powder described in co-pending European patent application ep 99300571.9 improves the properties of tablets, which are produced from mixtures of direct compressible starch, lactose and microcrystalline cellulose as excipients and 40% Paracetamol as active ingredient by direct compression.

Additionally the example demonstrates that the tablets obtained from mixtures of the directly compressible processed starch powder described in co-pending European patent application ep 99300571.9 and other excipients still have better properties compared to tablets obtained from mixtures of a conventional compressible starch and other excipients in the same conditions when Paracetamol is formulated with them.

Tablets containing 40% of Paracetamol were formulated with direct compressible starch, lactose and microcrystalline cellulose in different proportions according to the following procedure. All ingredients were sieved over a 0.8 mm sieve. A maximum of the Paracetamol (BUFA—crystalline grade) is blended with an equal quantity of each other ingredients following the dilution method in a low-shear drum mixer for 10 min at 12 rpm. Then the possible remaining of Paracetamol and of the other ingredients are added together with 0.25% $SiO_2$ (Aerosil 200—Degussa) to reach the proportions of each formulations described in tables 4 to 6 and blended for 15 min at 12 rpm. Afterwards 0.50% MgSt (Pharmachemic Tramedico) are added and blended for 3 min at 12 rpm. Round flat-faced tablets were compressed on a triple punch rotative tabletting press (Korch) operating at 40 rpm. The produced tablets have a surface of 1cm$^2$ and a target weight of 350 mg. The dimensions of the tablets and the hardness were measured with a tablet tester (ERWEKA, Model TBH). The friability of the tablets was determined on a friability tester (Pharmatest). The disintegration time was measured at 37° C. with a disintegration machine (ERWEKA, model ZT 73). The results are summarised as shown in tables 4 to 6.

TABLE 4

| Ratio of excipients + 40% Paracetamol (BUFA) | | | Tensile strength (N/mm$^2$)* at compression force 25kN | |
|---|---|---|---|---|
| MCC: Avicel PH-102 (FMC) | LACTOSE: Flowlac 100 (Meggle) | DC STARCH | With processed white maize starch* as DC Starch | With Starch 1500 ™ ** (Colorcon) as DC Starch |
| 1.0 | 0 | 0 | 4.6 | 4.6 |
| 0 | 1.0 | 0 | 1.3 | 1.3 |
| 0 | 0 | 1.0 | 1.8 | 0.9 |
| 0 | 0.50 | 0.50 | 1.4 | 1.0 |
| 0.50 | 0 | 0.50 | 2.7 | 2.2 |
| 0.50 | 0.50 | 0 | 2.5 | 2.5 |
| 0.20 | 0.20 | 0.60 | 1.7 | 1.3 |
| 0.20 | 0.60 | 0.20 | 1.6 | 1.5 |
| 0.60 | 0.20 | 0.20 | 2.8 | 2.6 |
| 0.33 | 0.33 | 0.34 | 1.8 | 1.7 |

*A processed white maize starch as described in co-pending European patent application ep 99300571.9
**Starch 1500 ™ HM from Colorcon Company Table 4 shows that tablets containing 40% of Paracetamol formulated with microcrystalline cellulose, lactose and the direct compressible processed starch described in co-pending European patent application ep 99300571.9 show in any proportion significantly higher tensile strengths than tablets containing 40% of Paracetamol formulated with microcrystalline cellulose, lactose and a standard direct compressible starch (Starch 1500 HM). Furthermore, tablets containing 40% of Paracetamol formulated with microcrystalline cellulose and the direct compressible processed starch described in co-pending European patent application ep 99300571.9 have a higher tensile strengths than tablets containing 40% of Paracetamol formulated with microcrystalline cellulose and lactose in respectively the same proportion. It is remarkable to notice that tablets containing 40% of Paracetamol formulated with microcrystalline cellulose and a standard direct compressible starch (Starch 1500 HM) show lower tensile strengths than tablets containing 40% of Paracetamol formulated with microcrystalline cellulose and lactose in respectively the same proportion.

This demonstrates that the directly compressible processed starch described in co-pending European patent application ep 99300571.9 does not decrease or even improves the quality of tablets in terms of hardness when it is used in mixtures with other excipients for the formulation of tablets containing 40% of Paracetamol.

TABLE 5

| Ratio of excipients + 40% Paracetamol (BUFA) | | | Friability (%) at compression force 25kN | |
|---|---|---|---|---|
| MCC: Avicel PH-102 (FMC) | LACTOSE: Flowlac 100 (Meggle) | DC STARCH | With processed white maize starch* as DC Starch | With Starch 1500 ™ ** (Colorcon) as DC Starch |
| 1.0 | 0 | 0 | 0.1 | 0.1 |
| 0 | 1.0 | 0 | 2.5 | 2.5 |
| 0 | 0 | 1.0 | 0.4 | 1.5 |
| 0 | 0.50 | 0.50 | 0.6 | 1.2 |
| 0.50 | 0 | 0.50 | 0.3 | 0.3 |
| 0.50 | 0.50 | 0 | 0.3 | 0.3 |
| 0.20 | 0.20 | 0.60 | 0.2 | 0.6 |
| 0.20 | 0.60 | 0.20 | 0.3 | 0.5 |
| 0.60 | 0.20 | 0.20 | 0.1 | 0.1 |
| 0.33 | 0.33 | 0.34 | 0.4 | 0.4 |

*A processed white maize starch as described in co-pending European patent application ep 99300571.9
**Starch 1500 ™ standard moisture from Colorcon Company Table 5 shows that tablets containing 40% of Paracetamol formulated with microcrystalline cellulose, lactose and the direct compressible processed starch described in co-pending European patent application ep 99300571.9 show in most proportions lower friability than tablets containing 40% of Paracetamol formulated with microcrystalline cellulose, lactose and a standard direct compressible starch (Starch 1500 HM). This demonstrates that the directly compressible processed starch described in co-pending European patent application ep 99300571.9 does not increase or even improves the quality of tablets in terms of friability when it is used in mixtures with other excipients for the formulation of tablets containing 40% of Paracetamol. The formulation of 40% Paracetamol with blends of the directly compressible processed starch described in co-pending European patent application ep 99300571.9, lactose and microcrystalline cellulose in any proportions yields tablets always within the limit of 1% friability recommended by the European Pharmacopoeia which is not the case when a standard direct compressible starch (Starch 1500 HM) is used.

TABLE 6

| Ratio of excipients + 40% Paracetamol (BUFA) | | | Disintegraation time (sec) at compression force 25kN | |
|---|---|---|---|---|
| MCC: Avicel PH-102 (FMC) | LACTOSE: Flowlac 100 (Meggle) | DC STARCH | With processed white maize starch* as DC Starch | With Starch 1500 ™ ** (Colorcon) as DC Starch |
| 1.0 | 0 | 0 | 50 | 50 |
| 0 | 1.0 | 0 | 105 | 105 |
| 0 | 0 | 1.0 | 115 | 505 |
| 0 | 0.50 | 0.50 | 40 | 80 |
| 0.50 | 0 | 0.50 | 60 | 140 |
| 0.50 | 0.50 | 0 | 50 | 50 |
| 0.20 | 0.20 | 0.60 | 55 | 140 |
| 0.20 | 0.60 | 0.20 | 30 | 40 |
| 0.60 | 0.20 | 0.20 | 55 | 80 |
| 0.33 | 0.33 | 0.34 | 40 | 60 |

*A processed white maize starch as described in co-pending European patent application ep 99300571.9
**Starch 1500 ™ standard moisture from Colorcon Company Table 6 shows that tablets containing 40% of Paracetamol formulated with microcrystalline cellulose, lactose and the direct compressible processed starch described in Co-pending European patent application ep 99300571.9 show in any proportion significantly faster disintegration times than tablets containing 40% of Paracetamol formulated with microcrystalline cellulose, lactose and a standard direct compressible starch (Starch 1500 HM).

This demonstrates that the directly compressible processed starch described in co-pending European patent application ep 99300571.9 significantly improves the quality of tablets in terms of faster disintegration time (from twice to 5 times faster) when it is used in mixtures with other excipients for the formulation of 40% Paracetamol containing tablet resulting in a faster liberation of the Paracetamol after ingestion of the tablet.

Figure 3B:
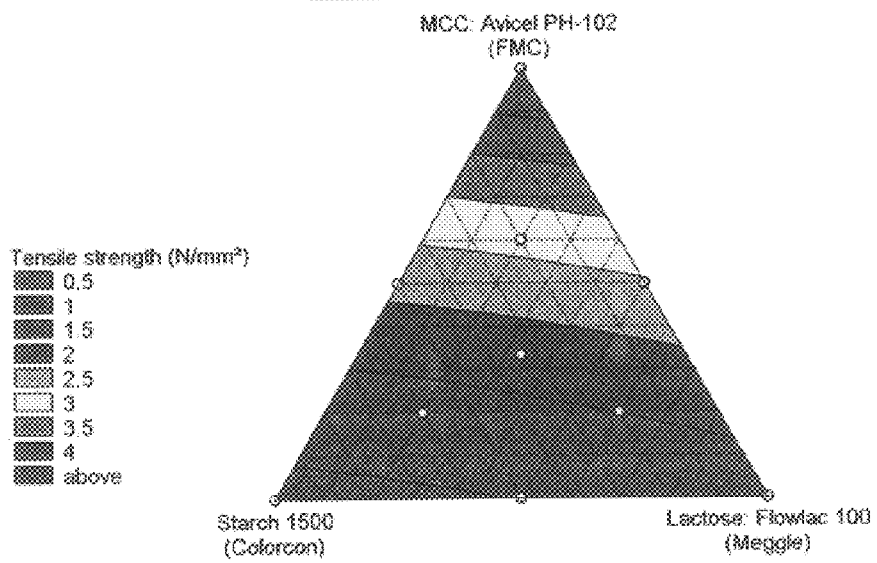

The results of tables 4 and 6 can be more easily illustrated by ternary graphs as shown in FIGS. 3 to 4. These ternary graphs are particularly helpful to examine the influence of the composition of the mixture on a pharmaceutical formulation. Response surface method is used to characterise the relationship between the ratio of excipients and the different tablet properties. It is also particularly powerful to identify potential synergies between the components of the mixtures. FIG. 3a compared with FIG. 3b shows that 40% Paracetamol tablets made from a mixture where besides microcrystalline cellulose and/or lactose also the directly compressible processed starch as described in Co-pending European patent application ep 99300571.9 is used, reaches in all the points a higher tensile strength than when a mixture where besides microcrystalline cellulose and/or lactose also a standard compressible starch is used. As in example 1, it is remarkable to notice that in FIG. 3a, the limiting factor in term of tensile strength of tablet is the proportion of lactose whereas, in FIG. 3b, this limiting factor is the proportion of standard direct compressible starch. This trend can also be noticed from the different orientation of the lines on each ternary graph.

Figure 4A:
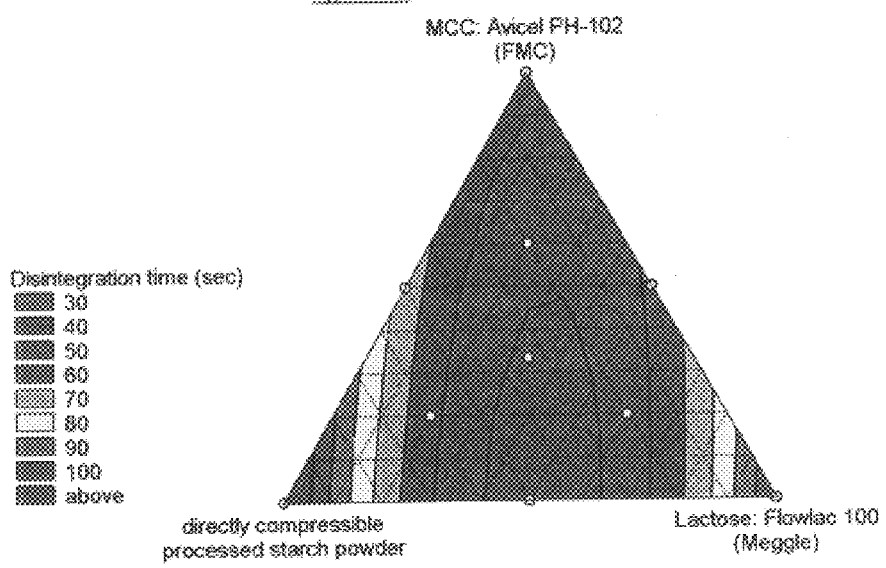
FIGS. 4a and 4b show the influence of the same compositions as demonstrated in FIGS. 3a and 3b, this time on the disintegration time.
Figure 4B:
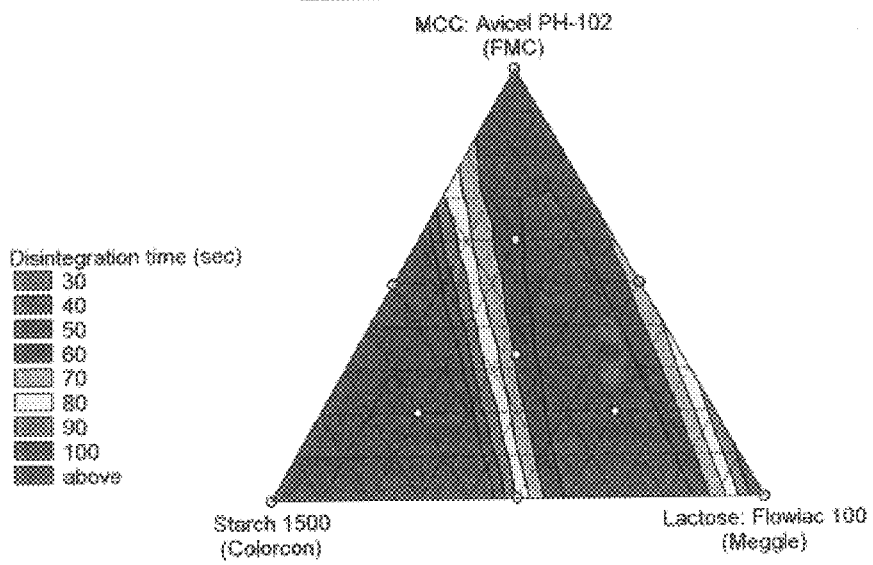

As in example 1, FIG. 4a compared with FIG. 4b shows that tablets made from a mixture where besides microcrystalline cellulose and/or lactose also the directly compressible processed starch as described in Co-pending European patent application ep 99300571.9 is used, reaches in all the points a lower disintegration time than when a mixture where besides microcrystalline cellulose and/or lactose also a standard compressible starch is used.

It is also remarkable to notice that in FIG. 4b, the limiting factor in term of disintegration time of tablet is by far the proportion of standard direct compressible. As long as more than 50% of standard direct compressible starch is used, the disintegration time of the tablets is never lower than 100 sec.

On the contrary, FIG. 4b reveals a parity in the effect of the directly compressible processed starch as described in Co-pending European patent application ep 99300571.9 and the lactose when used in the formulation, the area where the disintegration time is less than 50 sec. is significantly larger than in FIG. 4b.

What is claimed is:

1. A composition for forming a tablet or other unit dosage form comprising regular and smooth partially-swollen and non-birefrigent granules of starch, together with non-swollen birefrigent granules of starch wherein the ratio of non-swollen birefrigent granules to swollen non-birefrigent granules is in the range of from 1:5 to 5:1; and at least one other excipient.

2. A composition according to claim 1, wherein said composition further comprises an active ingredient.

3. A composition according to claim 2, wherein the active ingredient is selected from the group consisting of pharmaceutically active materials, foodstuffs, detergents, enzymes and other proteins, dyes, fertilizers and herbicidal products.

4. A composition according to claim 2 or 3, wherein the active ingredient is present in an amount of from 0.01 to 80% (w/w).

5. A composition according to claim 1, wherein the number of other excipients is between 1 and 10.

6. A composition according to claim 1 characterised in that the starch has an average particle size greater than 50 µm and a moisture content of from 3 to 15% by weight.

7. A tablet or other unit dosage form comprising a regular and smooth partially-swollen non-birefrigent granules of starch, together with non-swollen birefrigent granules of starch wherein the ratio of non-swollen birefrigent granules to swollen non-birefrigent granules is in the range of from 1:5 to 5:1 and at last one other excipient.

8. A tablet or other unit dosage form according to claim 7 further comprising an active ingredient.

9. A composition according to claim 5, wherein said excipient comprises a binder, filler or disintegrant.

10. A composition according to claim 1, wherein said excipient is selected from the group consisting of starch, pregelatinised starch, polyvinylpyrrolidone, methylcellulose, microcrystalline cellulose, dicalcium phosphate, tricalcium phosphate, calcium carbonate, calcium sulphate, lactose, dextrose, sucrose, sorbitol and mannitol, and mixtures thereof.

11. A composition according to claim 9 or 10, wherein the ratio of the directly compressible starch and the excipient is from 1:10 to 10:1.

12. A composition according to claim 3, wherein said active ingredient is a foodstuff.

13. A composition according to claim 12, wherein said foodstuff is at least one of a confectionary product, an aroma agent or a sweetener.

14. A composition according to claim 2, wherein said active ingredient comprises a pharmaceutically active material.

15. A composition according to claim 2, wherein said active ingredient comprises a fertilizer product.

16. A composition according to claim 2, wherein said active ingredient comprises an enzyme or other protein.

17. A composition according to claim 2, wherein said active ingredient comprises a detergent.

18. A composition according to claim 3, wherein said excipients are selected from the group consisting of starch, pregelatinised starch, polyvinylpyrrolidone, methylcellulose, microcrystalline cellulose, dicalcium phosphate, tricalcium phosphate, calcium carbonate, calcium sulphate, lactose, dextrose, sucrose, sorbitol, mannitol and mixtures thereof.

19. A tablet or other unit dosage form according to claim 7, wherein the starch has an average particle size greater than 50 µm and a moisture content of 3 to 15% by weight.

20. A tablet or other unit dosage form according to claim 8, wherein said active ingredient is present in an amount of 0.01 to 80% (w/w).

* * * * *